United States Patent [19]

Kneip et al.

[11] Patent Number: 5,530,159
[45] Date of Patent: Jun. 25, 1996

[54] PREPARATION OF α-ALANINEDIACETIC ACID OR ITS ALKALI METAL OR AMMONIUM SALTS

[75] Inventors: Michael Kneip, Frankenthal; Juergen Schneider, Freinsheim; Alfred Oftring, Bad Durkheim, all of Germany

[73] Assignee: BASF Aktiengesellschaft, Ludwigshafen, Germany

[21] Appl. No.: 318,882

[22] PCT Filed: May 12, 1993

[86] PCT No.: PCT/EP93/01171

§ 371 Date: Oct. 21, 1994

§ 102(e) Date: Oct. 21, 1994

[87] PCT Pub. No.: WO93/23363

PCT Pub. Date: Nov. 25, 1993

[30] Foreign Application Priority Data

May 20, 1992 [DE] Germany .......................... 42 16 560.1

[51] Int. Cl.$^6$ ................................................. C07C 229/00

[52] U.S. Cl. .............................................. 562/571; 562/576

[58] Field of Search ...................................... 562/571, 576

[56] References Cited

U.S. PATENT DOCUMENTS 5,068,416  11/1991  Baur et al. .............................. 562/571
5,130,476  7/1992   Baur et al. .............................. 562/571

*Primary Examiner*—José G. Dees
*Assistant Examiner*—Rosalynd A. Williams
*Attorney, Agent, or Firm*—Oblon, Spivak, McClelland, Maier & Neustadt

[57] ABSTRACT

The invention relates to a process for preparing β-alaninediacetic acid (Ia) or its alkali metal or ammonium salts (Ib) which comprises reacting iminodiacetic acid with acrylonitrile or $C_1$–$C_4$-alkyl acrylates in weakly acid to weakly basic aqueous medium and subsequently hydrolyzing the nitrile or ester moiety to the acid or a salt.

The products prepared according to the invention can be used, in particular, to form complexes.

3 Claims, No Drawings

PREPARATION OF α-ALANINEDIACETIC ACID OR ITS ALKALI METAL OR AMMONIUM SALTS

The preparation of β-alaninediacetic acid or its alkali metal or ammonium salts

The present invention relates to a novel process for preparing β-alaninediacetic acid (Ia) or its alkali metal or ammonium salts (Ib).

The compounds Ia and Ib are, just like nitrilotriacetic acid or ethylenediaminetetracetic acid and the salts of these amino polycarboxylic acids, important for forming complexes.

It is known to prepare β-alaninediacetic acid by reacting chloroacetic acid with β-alanine (G. Schwarzenbach et al., Helv. Chim. Acta 32 (1949), 1184). Also known are the cyanomethylation of β-alanine to give β-alaninediacetonitrile (V. G. Yashuniskii et al., Zh. Vses. Kim. Obschestva im D. I. Mendeleeva 10 (1965), 105) and the reaction of iminodiacetic acid with acrylamide to give β-alanine-N-acetamide-N-acetic acid (DE-A 27 27 755).

The two processes mentioned first require β-alanine, which is relatively difficult to obtain, as starting material and entail a plurality of stages, while the addition of iminodiacetic acid, which is easily obtained from ammonia, hydrocyanic acid and formaldehyde, onto acrylamide provides, just like the cyanomethylation of β-alanine, only a derivative of β-alaninediacetic acid, from which the acid is obtained only by subsequent hydrolysis of the cyano group or of the amide moiety.

Furthermore, DE-A 38 29 859 discloses a process for preparing β-alaninediacetic acid by reacting iminodiacetic with acrylic acid.

Since β-alaninediacetic acid and its salts are mainly used to form complexes, for example in detergents and cleaners, or in the photographic industry, as well as in cosmetic and pharmaceutical compositions, high purities are required.

Although equimolar reaction of iminodiacetic acid or its salts with acrylic acid gives high yields (up to 98% according to DE-A 38 29 859), the resulting products still contain unreacted acrylic acid and/or iminodiacetic acid or the salts thereof, which can be removed only with loss of yield, e.g. by recrystallization or by elaborate extraction processes. For the same reason, of course, it is inappropriate to use an excess of one starting material. The other processes, because of the reversibility of the Michael addition of iminodiacetic acid onto acrylic acid, likewise result in iminodiacetic and acrylic acid at the temperatures used (60° C.).

It is an object of the present invention to prepare the title compounds Ia and Ib by a simple and economic process without special purification steps with a purity such that the final product contains less than 0.5% iminodiacetic acid and less than 0.1% acrylic acid.

We have found that this object is achieved by a process for preparing β-alaninediacetic acid (Ia) or its alkali metal or ammonium salts (Ib) which comprises reacting iminodiacetic acid with acrylonitrile or $C_1$–$C_4$-alkyl acrylates in weakly acid to weakly basic aqueous medium and subsequently hydrolyzing the nitrile or ester moiety to the acid or a salt.

The iminodiacetic acid or its salts, especially the sodium or potassium salt, ought to have a minimum purity of about 95% by weight, preferably of about 99% by weight, since otherwise the purity of the final product might be impaired. However, iminodiacetic acid or its salts can easily be obtained in such purity even on the industrial scale.

The acrylonitrile or the acrylates are stabilized in a conventional way, e.g. with 50 ppm hydroquinone monomethyl ether or hydroquinone.

The reactants, iminodiacetic acid and acrylate or acrylonitrile, are expediently used in the molar ratio of from 1:0.95 to 1:2, preferably from 1:1.0 to 1:1.5.

The solvent is usually water. However, in the reaction of acrylates it is also possible to use a mixture of water and alcohol, preferably the alcohol corresponding to the acrylate used. An alcohol content of 20% by weight in the solvent mixture is adequate in this case.

The content of iminodiacetic acid in the complete aqueous mixture is generally from 10 to 40, preferably from 20 to 30, % by weight. The addition of the acrylate or of the acrylonitrile onto the iminodiacetic acid takes place at a distinct rate even below 0° C. and, at 20°–40° C., normally takes from 0.25 to 5 hours. The temperature is preferably maintained below 60° C.

Particularly suitable pH values are from 5 to 11, preferably from 6 to 8.

After the reaction it is expedient to pass a stream of air or inert gas, e.g. nitrogen, through the reaction mixture in order to distil out excess acrylate or acrylonitrile, which can be used again for further reactions.

The distillation is advantageously carried out under a pressure of from 100 to 1000 mbar. The temperature should not exceed 60° C. during this either.

This is followed, without isolation of the intermediates, by hydrolysis of the β-alaninediacetate or -diacetonitrile in alkaline or nitrogen as basic aqueous medium or in aqueous mineral acid medium. The pH of the aqueous solution can accordingly be in the range from 0 to 14, in particular from 4 to 9. If necessary, it is adjusted or kept constant with a mineral acid, for example sulfuric acid, hydrochloric acid, orthophosphoric acid or nitric acid in the acid hydrolysis, or with aqueous alkali, for example sodium hydroxide, potassium hydroxide, sodium bicarbonate or sodium carbonate, or a nitrogeneous base such as ammonia or triethylamine in the alkaline hydrolysis. The hydrolysis is expediently carried out at from 20° to 60° C. in particular from 40° to 60° C. No retroadditions are observed under these mild hydrolysis conditions. The reaction is usually complete after from 5 to 24 hours at from 40° to 60° C.

It is furthermore beneficial to pass a stream of air or inert gas, e.g. nitrogen, through the reaction mixture during the hydrolysis and to distil out the resulting alcohol and ammonia continuously in the form of aqueous solutions.

If required, the alkali metal or ammonium salts Ib can be obtained in solid form in a conventional way, e.g. by distilling out water and subsequently crystallizing or by spray drying.

If the intention is that one, two or, preferably three carboxyl groups of Ib are to be in free form, this is achieved by adding the appropriate amount of mineral acid to their salts. Examples of mineral acids which can be used are sulfuric acid, hydrochloric acid, orthophosphoric acid or nitric acid. From 20 to 100% by weight, in particular from 30 to 70% by weight, sulfuric acid has proven particularly beneficial.

This reaction is usually carried out at from 10° to 60° C., preferably from 20° to 50° C. The compounds I containing free carboxyl groups are expediently isolated by crystallization or precipitation. If the intention is to obtain β-alaninediacetic acid with three free carboxyl groups, the product is particularly advantageously precipitated by adding from 30 to 70% by weight sulfuric acid at a pH of from 1.5 to 2.5, in particular from 1.8 to 2.2. It is advisable to complete the precipitation or crystallization by subsequent cooling to from 0° to 35° C.

The process according to the invention can be carried out either batchwise or continuously.

The present invention also relates to the use of the β-alaninediacetic acid and its alkali metal salts I prepared by the process according to the invention to form complexes.

A process according to the invention makes it possible to prepare β-alaninediacetic acid and its alkali metal salts in highly pure form, i.e. greater than 99.5% by weight, and with less than 0.5% by weight of iminodiacetic and less than 0.1% by weight of acrylic acid, without additional purification steps in a simple and economic synthesis even on the industrial scale.

Moreover, the process according to the invention produces no interfering byproducts, and resulting acrylonitrile or acrylate and, possibly, alcohol can be reused, and resulting aqueous ammonia can easily be utilized elsewhere.

EXAMPLE 1

Preparation of trisodium β-alaninediacetate (ADA Na$_3$) (acrylonitrile route)

445.7 g of acrylonitrile (corresponding to 8.4 mol) were added dropwise over the course of one hour to 3540 g of a 40% by weight aqueous solution of disodium iminodiacetate (corresponding to 8 mol) at from 30° to 35° C. with stirring. Reaction was then allowed to continue at 30° C. for three hours. In the final hour, a vigorous stream of nitrogen was passed through the reaction solution, and a total of about 100 g of acrylonitrile/water mixture containing about 21 g of acrylonitrile was condensed.

Then, while stirring at 40° C. 648 g of 50% by weight sodium hydroxide solution (corresponding to 8.1 mol) were added dropwise over the course of 30 minutes. Four hours at 40° C. were followed by eight hours at 60° C.. During the addition of sodium hydroxide solution and the subsequent reaction, a vigorous stream of air was passed through the reaction solution, and a total of about 600 ml of aqueous ammonia were distilled out until the ammonia concentration in the reaction mixture reached 100 ppm. The resulting solution was adjusted with water to a concentration of 40% by weight trisodium β-alaninediacetate.

A representative sample was dried to constant weight under reduced pressure and analyzed:
ADA Na$_3$: 99.6%
Iminodiacetic acid content: 0.3%
Acrylic acid content <0.05%
Acrylonitrile content: <20 ppm

EXAMPLE 2

Preparation of β-alaninediacetic acid (acrylonitrile route)

A 40% by weight aqueous solution of trisodium β-alaninediacetate was prepared as in Example 1. 434 g of 50% by weight sulfuric acid were added dropwise to 1 kg of this solution stirred at from 20° to 40° C., which adjusted the pH to about 2.0. The mixture was subsequently cooled to 20° C. and stirred at this temperature for one hour. The precipitate was filtered off, washed with ice-water until a sulfate test on the washings with aqueous barium chloride solution was negative, and dried at 60° C. under reduced pressure. 284 g of the title compound were obtained, corresponding to a yield of 94%; the product melted at 205° C. with decomposition and had a purity of 99.9%.
Iminodiacetic acid content: <0.1%
Acrylic acid content: <0.05%
Sulfate content: <0.1 ppm

EXAMPLE 3

Preparation of trisodium β-alaninediacetate (acrylate route)

723.2 g of methyl acrylate (corresponding to 8.4 mol) were added dropwise over the course of one hour to 3540 g of a 40% by weight aqueous solution of disodium iminodiacetate (corresponding to 8 mol) at 20° to 30° C. with stirring. Reaction was then allowed to continue at 30° C. for four hours. In the final hour, a vigorous stream of nitrogen was passed through the reaction solution, and a total of about 160 g of methyl acrylate/water mixture were condensed, containing about 34 g of methyl acrylate.

To hydrolyze the ester, 648 g of 50% by weight sodium hydroxide solution (corresponding to 8.1 mol) were added dropwise over the course of 30 minutes while stirring at 40° C. The reaction solution was kept at 40° C. for a further ten hours. During the addition of sodium hydroxide solution and the subsequent reaction, a vigorous stream of air was passed through the reaction solution, and a total of about 250 ml of methanol and about 550 ml of water were distilled out. The resulting solution was adjusted with water to a content of 40% by weight of trisodium β-alaninediacetate.

A representative sample was dried to constant weight under reduced pressure and analyzed:
ADA Na$_3$: 99.6%
Iminodiacetic acid content: 0.2%
Acrylic acid content: <0.05%
Methyl acrylate content: <20 ppm
Methanol content: <50 ppm

EXAMPLE 4

Preparation of β-alaninediacetic acid (acrylate route)

A 40% by weight aqueous solution of trisodium β-alaninediacetate was prepared as in Example 3. 434 g of 50% by weight sulfuric acid were added dropwise to 1 kg of this solution stirred at 20° to 40° C. which adjusted the pH to about 2.0. The mixture was subsequently cooled to 20° C. and stirred at this temperature for one hour. The precipitate was filtered off, washed with ice-water until a sulfate test on the washings with aqueous barium chloride solution was negative, and dried at 60° C. under reduced pressure. 363 g of the title compound were obtained, corresponding to a yield of 98%; the product melted at 204°–205° C. with decomposition and had a purity of 99.9%.
Iminodiacetic acid content: <0.1%
Acrylic acid content: <0.05%
Methyl acrylate content: <0.01 ppm
Sulfate content: <0.1%

EXAMPLE 5

Preparation of disodium β-alaninediacetate (acrylate route)

1064 g of iminodiacetic acid (corresponding to 8 mol) were suspended in 2000 g of water, and 640 g of 50% by weight sodium hydroxide solution were added (pH about 7.0) to dissolve the iminodiacetic acid. 723.2 g of methyl acrylate (corresponding to 8.8 mol) were added dropwise over the course of one hour while stirring at from 20° to 30° C. The reaction was allowed to continue at 30° C for twelve hours. In the final hour, a vigorous stream of nitrogen was passed through the reaction solution, and a total of about 340 g of methyl acrylate/water mixture were condensed, this contained about 68 g of methyl acrylate.

Subsequently, 648 g of 50% by weight sodium hydroxide solution (corresponding to 8.1 mol) were added dropwise over the course of 30 minutes while stirring at 40° C., and the mixture was stirred at 40° C. for a further ten hours. During the reaction, a vigorous stream of air was passed through the reaction solution, and a total of about 800 g of methanol/water mixture, containing about 250 g of methanol, were distilled out. The resulting solution was adjusted with water to a content of 40% by weight of disodium β-alaninediacetate.

A representative sample was dried to constant weight under reduced pressure and analyzed:
ADA Na$_2$: 99.6%
Iminodiacetic acid content: 0.2%
Acrylic acid content: <0.05%
Methyl acrylate content: <20 ppm
Methanol content: <50 ppm

EXAMPLE 6

Preparation of trisodium β-alaninediacetate (acrylate route)

50 g of ethanol were added all at once, and subsequently 84.1 g of ethyl acrylate (corresponding to 0.84 mol) were added dropwise over the course of one hour to 708 g of a 20% by weight aqueous solution of disodium iminodiacetate (corresponding to 0.8 mol) while stirring at from 20° to 30° C. The reaction was then allowed to continue at 30° C for five hours. In the last two hours, a vigorous stream of nitrogen was passed at 800 mbar and 30° C. through the reaction solution, and a total of about 135 g of ethyl acrylate/ethanol/water mixture were condensed, which contained about 4.0 g of ethyl acrylate and 50 g of ethanol. Then, while stirring at 40° C., 64.8 g of 50% by weight sodium hydroxide solution (corresponding to 0.81 mol) were added dropwise over the course of 30 minutes, and the reaction solution was kept at 40° C. for a further ten hours. During the addition of sodium hydroxide solution and the reaction, a vigorous stream of air was passed through the reaction solution, and a total of about 36.8 g of ethanol and about 85 g of water were distilled out. The resulting solution was adjusted with water to a content of 20% by weight trisodium β-alaninediacetate.

A representative sample was dried to constant weight under reduced pressure and analyzed:
ADA Na$_3$: 99.6%
Iminodiacetic acid content: 0.2%
Acrylic acid content: <0.05%
Ethyl acrylate content: <20 ppm
Ethanol content: <50 ppm
Sulfate content: <0.1%

We claim:

1. A process for preparing β-alaninediacetic acid (Ia) or its alkali metal or ammonium salts (Ib) which comprises reacting iminodiacetic acid with acrylonitrile or $C_1$–$C_4$-alkyl acrylates in aqueous medium at a p.H of from 5 to 11 and subsequently hydrolyzing the nitrile or ester moiety to the acid or a salt.

2. The process of claim 1, wherein the temperature of said reaction of iminodiacetic acid with acrylonitrile or $C_1$–$C_4$-alkyl acrylate is maintained at ≦60° C.

3. The process of claim 1, wherein said reaction of iminodiacetic acid with acrylonitrile or $C_1$–$C_4$-alkyl acrylate is carried out at a pH of from 6 to 8.

* * * * *